United States Patent
Kitajima (10) Patent No.: US 7,023,613 B2
(45) Date of Patent: Apr. 4, 2006

(54) OPERATION MICROSCOPE AND OBSERVATION PRISM

(75) Inventor: Nobuaki Kitajima, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/890,229

(22) Filed: Jul. 14, 2004

(65) Prior Publication Data
US 2005/0012992 A1    Jan. 20, 2005

(30) Foreign Application Priority Data
Jul. 18, 2003   (JP)   ............... 2003-198919

(51) Int. Cl.
  *G02B 21/00*   (2006.01)
(52) U.S. Cl. .............. 359/381; 359/837; 351/216
(58) Field of Classification Search ............... 359/368, 359/381, 831, 837; 351/205, 216, 221
See application file for complete search history.

(56) References Cited

U.S. PATENT DOCUMENTS

| | | | | |
|---|---|---|---|---|
| 4,478,499 A | * | 10/1984 | Hoerenz | 351/211 |
| 6,118,597 A | | 9/2000 | Maruyama | 359/743 |
| 6,476,851 B1 | | 11/2002 | Nakamura | 348/65 |
| 6,788,455 B1 | * | 9/2004 | Kirchhuebel et al. | 359/381 |
| 2002/0191280 A1 | | 12/2002 | Horiguchi et al. | 359/383 |

FOREIGN PATENT DOCUMENTS

JP    2003-62003    3/2003

\* cited by examiner

*Primary Examiner*—Mark A. Robinson
(74) *Attorney, Agent, or Firm*—Armstrong, Kratz, Quintos, Hanson & Brooks, LLP (57) ABSTRACT

There are provided an operation microscope and an observation prism which are capable of conducting a high-visibility observation with less glare. The operation microscope includes an objective lens opposed to an eye to be operated, a front lens which is provided between the eye to be operated and an anterior focal point of the objective lens and condenses illumination light to illuminate an interior of the eye to be operated, and the observation prism disposed near the front lens to observe fundus and its surroundings of the eye to be operated. An oblique surface (refractive surface) of the observation prism has a curved shape in which the curved shape shows a certain negative curvature in a direction to an intersection with a refractive surface. Therefore, aberrations caused on images of entrance pupils of an observation system and an image of an exit pupil of an illumination system can be corrected. The images of the entrance pupils and the image of the exit pupil are sufficiently separated from one another on a cornea of the eye to be operated, so that an observation with less glare can be conducted.

5 Claims, 7 Drawing Sheets

PRIOR ART

FIG. 9(A)

PRIOR ART

FIG. 9(B)

PRIOR ART

PRIOR ART

OPERATION MICROSCOPE AND OBSERVATION PRISM

BACKGROUND OF THE INVENTION

1. Field of the Invention

The present invention relates to an operation microscope and an observation prism in an ophthalmologic field. In particular, the present invention relates to an operation microscope which is provided with a front lens for observing a fundus of an eye to be operated and an observation prism disposed near the front lens to observe fundus and its surroundings of the eye to be operated during a vitreous body operation or the like, and the, observation prism used in the operation microscope.

2. Description of the Related Art

An operation in an ophthalmologic field is generally conducted with a microscope observation. An example of an operation microscope used in the ophthalmologic field is disclosed in JP 2003-062003 A. The operation microscope disclosed therein is constructed such that the front lens is removably inserted between (anterior focal position of) an objective lens and the eye to be operated. The front lens has refracting power of about 30 diopters (D) to 50 diopters (D) and is disposed to condense illumination light, thereby guiding the illumination light to the interior of the eye to be operated. Using the front lens enables an operation in a state where operational instruments are held with both hands.

An observation prism for observing fundus and its surroundings of the eye to be operated is rotatably provided near the front lens of the operation microscope described in JP 2003-062003 A. A bottom surface and an oblique surface of the observation prism each are formed flat.

Figure 8:
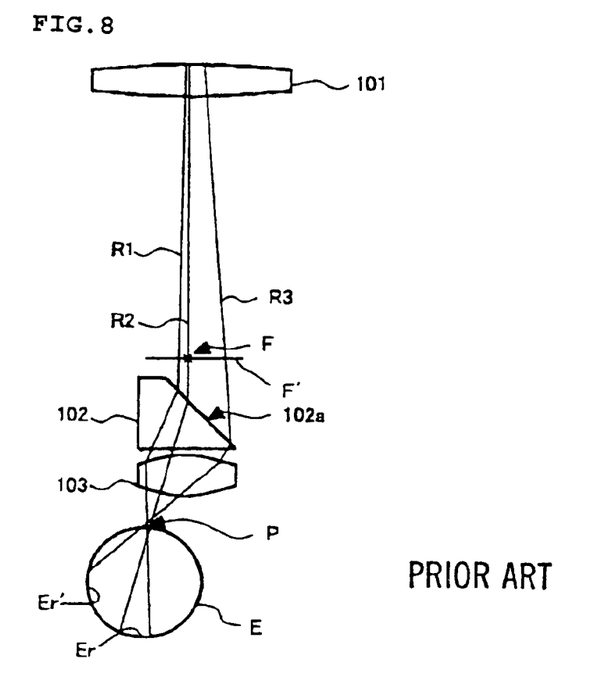
FIG. 8 is a schematic view showing an imaging state of the entrance pupil of the observation system in the case where the fundus and its surroundings of the eye to be operated are being observed in a state where a conventional observation prism is disposed.
Figure 9A:
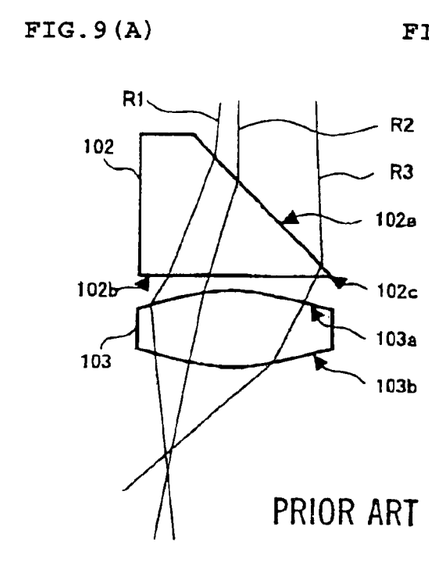
FIG. 9A is a partially enlarged side view showing the front lens and the conventional observation prism of FIG. 8
Figure 9B:
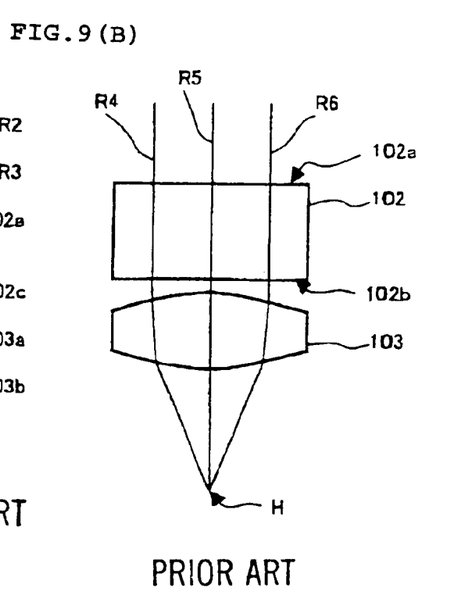
FIG. 9B is a cross sectional view in a direction orthogonal to a paper surface of FIG. 9A.

FIGS. 8, 9A, and 9B are schematic views showing a part of an optical system included in the above-mentioned conventional operation microscope. FIG. 8 is a side view showing an imaging state of an entrance pupil of an observation optical system in the case where the fundus and its surroundings of the eye to be operated are being observed using the above-mentioned observation prism. FIG. 9A is a partially enlarged side view showing the front lens and the observation prism which are shown in FIG. 8. FIG. 9B is a cross sectional view showing the front lens and the observation prism in a direction orthogonal to a paper surface in FIG. 9A.

As shown in FIG. 8, the conventional operation microscope is constructed so as to observe fundus and its surroundings Er' of an eye to be operated E in a state where an observation prism 102 is disposed between an anterior focal point F of an objective lens 101 and a front lens 103. Note that the fundus and its surroundings Er' indicate surrounding regions of a fundus Er of the eye to be operated E. Reference symbol F' in FIG. 8 indicates an intermediate image plane on which an image of the fundus Er is formed.

As shown in FIGS. 9A and 9B, light beams are refracted on two refractive surfaces 102a and 102b of the observation prism 102 to change traveling directions of those. The two refractive surfaces 102a and 102b each are formed flat (that is, curvature is 0). The observation prism 102 is constructed such that the refractive surface (oblique surface) 102a has a predetermined oblique angle with respect to the refractive surface 102b. Note that the predetermined oblique angle is angle at an intersection (prism apex) 102c of the two refractive surfaces 102a and 102b.

In FIGS. 8, 9A, and 9B, principle rays R1, R2, and R3 corresponding to observation points of the eye to be operated E are shown. As enlargedly shown in FIG. 9A, when the light beams are transmitted through the observation prism 102, the light beams are significantly refracted on the oblique surface 102a and then refracted on the refractive surface 102b. After that, the light beams are incident on the front lens 103 at a large angle with respect to the optical axis direction of the front lens 103. Therefore, a large aberration is caused in the refracting direction, so that the entrance pupil of the observation optical system located above the objective lens 101 is not clearly imaged on the cornea of the eye to be operated E to be blurred. Although not shown here, an image of the exit pupil of an illumination system for emitting illumination light similarly is blurred.

On the other hand, as shown in FIG. 9B, an aberration is not caused in a direction orthogonal to the oblique direction, so that principle rays R4, R5, and R6 are condensed at a point H.

Figure 10A:
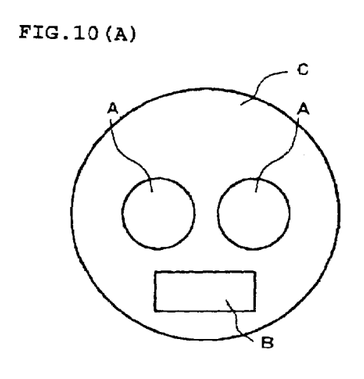
FIG. 10A is a schematic view showing imaging states of images related to entrance pupils of the observation system and an imaging state of an image related to the exit pupil of the illumination system on a cornea of the eye to be operated, which shows a state in which those images are separated from one another by the operation microscope of the present invention.

When an observation is conducted with a less glare state, it is necessary to separate an illumination light flux from and an observation light flux on the cornea of the eye to be operated E. That is, as shown in FIG. 10A, it is necessary to clearly separate images A of the entrance pupils of the observation system from an image B of the exit pupil of the illumination system on a cornea C.

Figure 10B:
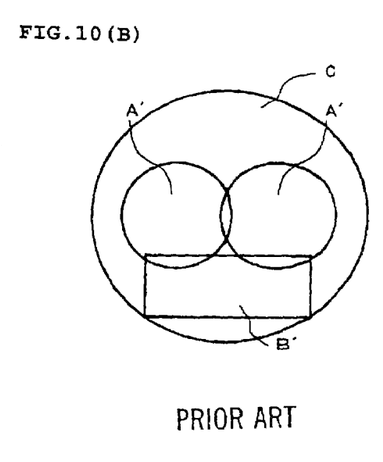
FIG. 10B shows a conventional case where the images overlap with one another.

However, according to the conventional operation microscope, as described above, imaging states of the entrance pupils of the observation system and an imaging state of the exit pupil of the illumination system are poor. That is, as shown in FIG. 10B, images A' of the entrance pupils and an image B' of the exit pupil are formed on the cornea C with blurred states. Therefore, the images A' and the image B' overlap with one another, so that the images A' and the image B' are not clearly separated from one another. Thus, the observation light is mixed with a glare, an observation with high visibility cannot be conducted.

SUMMARY OF THE INVENTION

The present invention has been made in view of the above-mentioned circumstances. An object of the present invention is to provide an operation microscope for correcting an aberration caused when an observation prism is used, in which an imaging state of an entrance pupil of an observation system and an imaging state of an exit pupil of an illumination system are improved, so that a high-visibility observation with less glare can be conducted.

Also, another object of the present invention is to provide an observation prism capable of observing fundus and its surroundings with less glare when used for an operation microscope.

In order to attain the above-mentioned objects, according to a first aspect of the present invention, there is provided an operation microscope, including: an objective lens opposed to an eye to be operated; a front lens for condensing illumination light to illuminate an interior of the eye to be operated, which is provided between the eye to be operated and an anterior focal point of the objective lens; and an observation prism for refracting the illumination light on two refractive surfaces to illuminate fundus and its surroundings of the eye to be operated, which is removably inserted between the anterior focal point of the objective lens and the front lens, in which the operation microscope is characterized in that at least one of the two refractive surfaces of the observation prism is formed in a curved shape in which said curved shape shows a certain negative curvature in a direction to an intersection of the two refractive surfaces.

Also, in order to attain a second aspect of the present invention, in the operation microscope according to the first aspect of the invention, the operation microscope is characterized in that said certain negative curvature is variable curvature.

Also, in order to attain the above-mentioned objects, according to a third aspect of the present invention, in the operation microscope according to the first aspect of the invention, the operation microscope is characterized in that one of the two refractive surfaces of the observation prism is formed in the curved shape in which a curvature along a direction orthogonal to the direction to the intersection shows 0.

Also, in order to attain the above-mentioned objects, according to a fourth aspect of the present invention, in the operation microscope according to the first or second aspect of the invention, the operation microscope is characterized in that one of the two refractive surfaces of the observation prism is formed in the curved shape in which the curved shape shows a negative curvature at a constant rate in the direction to the intersection.

Also, in order to attain the above-mentioned objects, according to a fifth aspect of the present invention, there is provided an observation prism which is disposed between an anterior focal point of an objective lens and a front lens of an operation microscope including the front lens for condensing illumination light to illuminate an interior of an eye to be operated, the front lens being provided between the eye to be operated and the anterior focal point of the objective lens, and used for refracting the illumination light on two refractive surfaces to illuminate fundus and its surroundings of the eye to be operated, in which the observation prism is characterized in that at least one of the two refractive surfaces is formed in a curved shape in which the curved shape shows a certain negative curvature in a direction to an intersection of the two refractive surfaces.

DETAILED DESCRIPTION OF THE PREFERRED EMBODIMENT

Hereinafter, an example of an operation microscope according to an embodiment of the present invention will be described in detail with reference to the drawings.

[Entire Structure of Operation Microscope]

Figure 1:
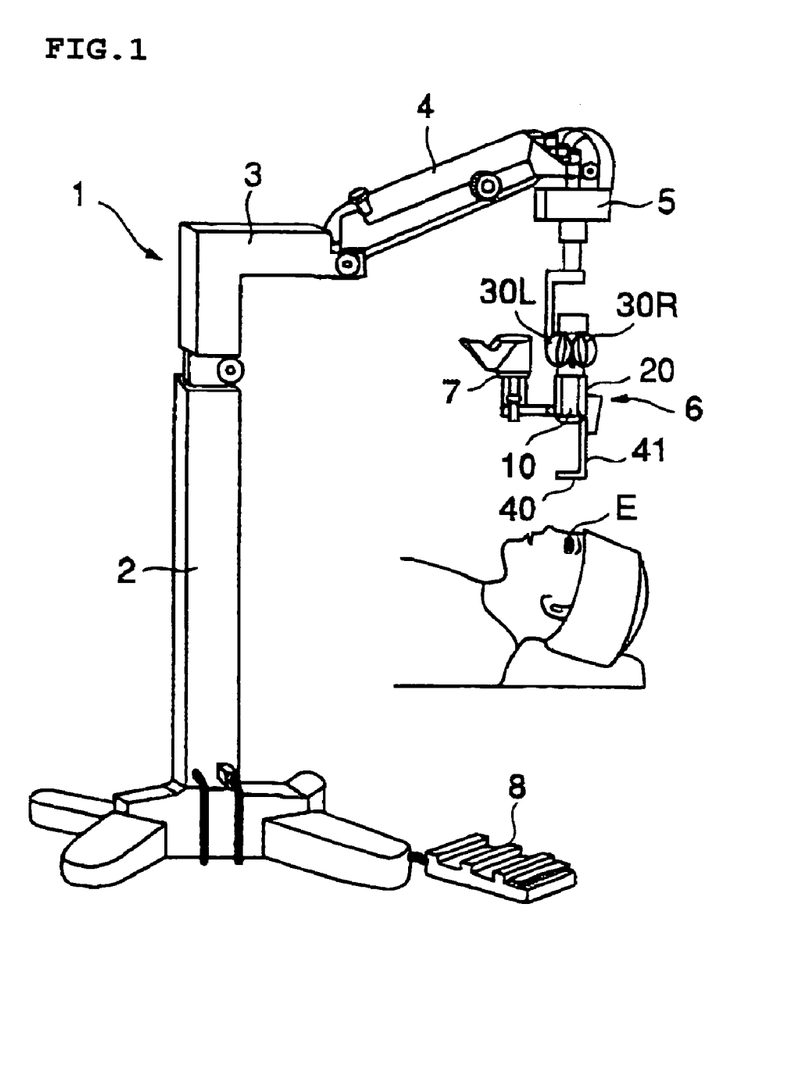
FIG. 1 is an external view showing an entire schematic structure of an operation microscope according to an embodiment of the present invention.

FIG. 1 shows an entire structure of an operation microscope 1 according to this embodiment. The operation microscope 1 includes: a pillar 2 for supporting the entire operation microscope 1; a first arm 3 whose one end is connected with an upper end of the pillar 2; a second arm 4 whose one end is connected with the other end of the first arm 3; a drive device 5 connected with the other end of the second arm 4; an operator's microscope 6 suspended from the drive device 5; an assistant's microscope 7 provided adjacent to the operator's microscope 6; and a foot switch 8 for conducting various manipulations by a foot. The operator's microscope 6 and the assistant's microscope 7 are three-dimensionally driven in a lateral direction and a horizontal direction by the drive device 5. Reference symbol E denotes an eye of a patient who undergoes an operation (eye to be operated). Reference numeral 40 denotes a front lens disposed between an objective lens (described later) of the operator's microscope 6 and the eye to be operated E.

[Structure of Operator's Microscope]

Figures 2A, 2B, 2C:
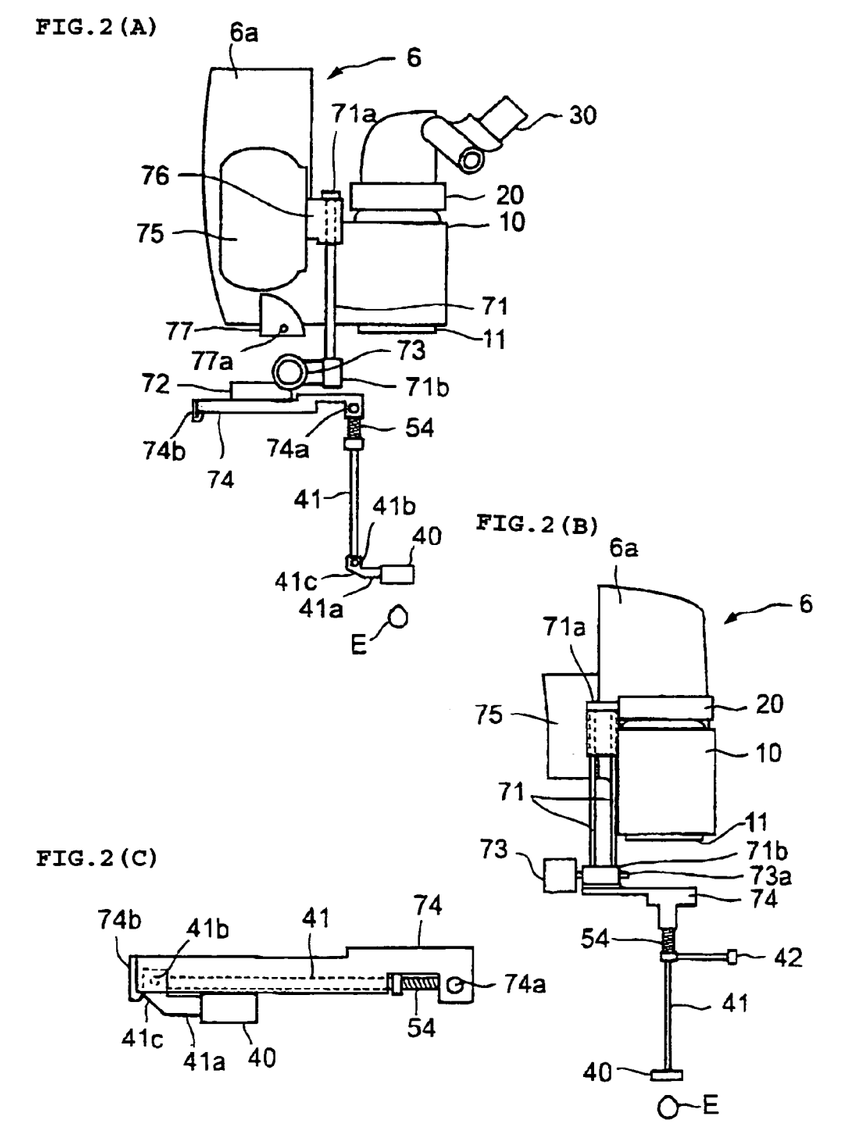
FIG. 2A is an enlarged external side view showing a schematic structure of an operator's microscope of the operation microscope according to the embodiment of the present invention.
FIG. 2B is an external front view of FIG. 2A.
FIG. 2C is a perspective side view showing a storing state of a front lens of FIG. 2A.

FIGS. 2A, 2B, and 2C are enlarged explanatory views showing a structure of the operator's microscope 6, in which FIG. 2A is an external side view thereof, FIG. 2B is an external front view thereof, and FIG. 2C is a perspective side view showing a storing state of the front lens 40. As shown in FIGS. 2A and 2B, the operator's microscope 6 includes a main body part 6a, a lens barrel part 10, an inverter section 20, and a pair of left and right eyepieces 30 (30L and 30R in FIG. 1). In FIG. 2B, the eyepieces 30 are omitted. The front lens 40 is connected with the main body part 6a through a holding arm 41 and the like and provided to be insertable between the above-mentioned objective lens and the eye to be operated E (details of the front lens 40 are described later).

Although not shown, the main body part 6a includes a control circuit for controlling the operation of the operator's microscope 6, a micro-motion drive device for moving the lens barrel part 10 upward and downward by the control circuit, and the like. The lens barrel part 10 includes an objective lens 11 opposed to the eye to be operated E, a known illumination system for irradiating the eye to be operated E with illumination light, and a known observation system for observing the eye to be operated E illuminated by the illumination system. The inverter section 20 includes a known optical unit for converting an image observed as an inverted image to an erect image.

[Structure of Front Lens and Portions Surrounding the Front Lens]

A structure of the front lens 40 and portions surrounding the front lens will be described. As described above, the front lens 40 is connected with the operator's microscope 6 through the holding arm 41 and the like. The front lens 40 is mounted to a holding plate 41a formed at the tip end of the holding arm 41.

The holding arm 41 and the holding plate 41a are connected with each other to be pivotable on a pivot 41b. An oblique portion 41c is provided in the holding plate 41a. A front lens operating knob 42 for pivoting the holding arm 41 is provided in the holding arm 41.

The operator's microscope 6 further includes: an elevating arm 71 having a fringe portion 71a on an upper side thereof; a connecting part 71b connected with a lower portion of the elevating arm 71; an elevation regulating member 72 connected with the connecting part 71b; a connecting knob 73 extended through the connecting part 71b; and a storing part 74 that is provided to be attachable to the elevation regulating member 72 and stores the front lens 40 and the holding arm 41. The holding arm 41 is provided in the storing part 74 to be pivotable on a pivot 74a. A coil spring 54 is mounted on an upper portion of the holding arm 41 as in FIG. 2A. Note that the storing part 74 is provided to be attachable to the elevation regulating member 72 because, for example, it is necessary to detach the front lens 40 and the holding arm 41 in order to perform sterilization processing after the operation and the like. The operation microscope in which the front lens 40 and the like are detached can be used as a general operation microscope. Hereinafter, the respective members described in this paragraph are collectively called a front lens supporting part in some cases.

A drive section 75 for driving an elevating arm support member 76 supporting the elevating arm 71 upward and downward is provided on the main body part 6a of the operator's microscope 6. The elevating arm 71 is extended through the elevating arm support member 76. The elevating arm 71 is prevented from being separated from the elevating arm support member 76 by the fringe portion 71a. As a result, the front lens 40 is moved upward and downward according to the up-and-down movement of the elevating arm support member 76, which is caused by the drive section 75. Therefore, a distance between the front lens and the objective lens 11 is relatively changed. According to such a structure, it is possible to move only the front lens 40 upward and downward without being associated with the up-and-down micro-motion of the lens barrel part 10.

An elevation regulating member 77 for regulating an upward movable range of the front lens supporting part with the elevation regulating member 72 is mounted on a lower portion of the main body part 6a. A connecting hole 77a for fixedly connecting the front lens supporting part to the main body part 6a by operating the connecting knob 73 is formed in the elevation regulating member 77. Note that the front lens supporting part is connected with the main body part 6a in the following manner. The front lens supporting part is elevated up to the uppermost position by the drive section 75 (at this time, a convex portion 73a of the connecting knob 73 is aligned with the connecting hole 77a). After that, the convex portion 73a is inserted into the connecting hole 77a by rotating the connecting knob 73 in a predetermined direction.

FIGS. 2A and 2B show a state in which the front lens 40 of the operator's microscope 6 is inserted between the eye to be operated E and the objective lens 11 (a state when the operation microscope is used). When an operator stops using the front lens 40 and moves the front lens out of an optical path, the operator grasps the front lens operating knob 42 and pivots the holding arm 41 upward on the pivot 74a to store the front lens 40 and the holding arm 41 in the storing part 74. On the other hand, when the front lens 40 stored in the storing part 74 is to be used, the operator grasps the front lens operating knob 42 and the holding arm 41 is pivoted downward on the pivot 74a.

FIG. 2C shows a state in which the front lens 40 is stored in the storing part 74 (storing position). As shown in FIG. 2C, the front lens 40 and the holding arm 41 which are pivoted on the pivot 74a upward are stored in the storing part 74 along the longitudinal direction thereof. The holding plate 41a is stored in a bent state by pivoting on the pivot 41b. This results from the action between the oblique portion 41c of the holding plate 41a and a contact member 74b mounted on an end portion of the storing part 74. That is, when the holding arm 41 is pivoted upward, the oblique portion 41c is in contact with the contact member 74b and the holding plate 41a is guided along the oblique portion 41c to pivot on the pivot 41b, so that the holding plate 41a is automatically bent and stored.

[Structure of Optical System of Operator's Microscope]

Next, an optical system included in the operator's microscope will be described with reference to a schematic side view of the optical system of FIG. 3. The objective lens barrel part 10 includes the objective lens 11 opposed to the eye to be operated E, a zoom lens 12, and an illumination prism 13. The front lens 40 is inserted between the eye to be operated E and an anterior focal point F of the objective lens 11. Here, a posterior focal point of the front lens 40 is identical to the anterior focal point F of the objective lens 11.

The zoom lens 12 is an optical element composing a part of the observation system, which is used for changing a magnification of an observation image. Although not shown, the observation system including the zoom lens 12 is composed of a left observation system for guiding an observation light flux to the eyepiece 30L and a right observation system for guiding an observation light flux to the eyepiece 30R. An entrance pupil of the observation system is formed at a position between the objective lens 11 and the zoom lens 12.

The illumination prism 13 is a prism member disposed at a position eccentric from an optical axis (observation axis) O of the objective lens 11, which is used to deflect illumination light from the illumination system which is not shown to illuminate the eye to be operated E. The exit pupil of the illumination system is formed on the refractive surface of the illumination prism 13.

[Structure of Observation Prism and Operation thereof]

Figure 4:
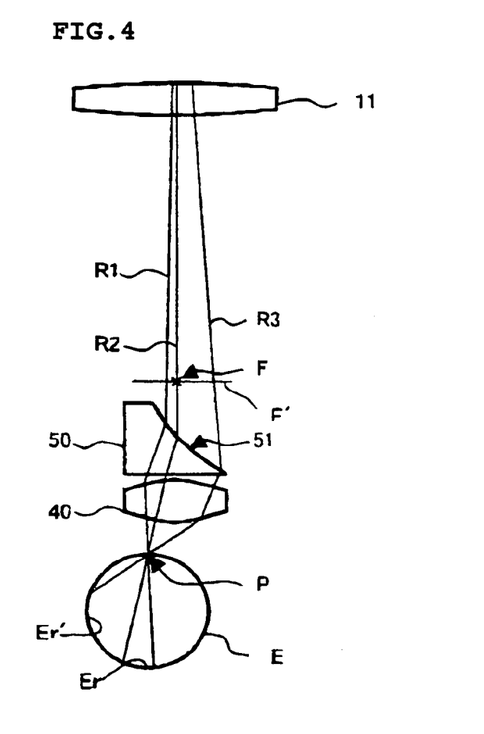
FIG. 4 is a schematic view showing an imaging state of an entrance pupil of an observation system in the case where fundus and its surroundings of an eye to be operated are being observed in a state where an observation prism is disposed.
Figures 5A, 5B:
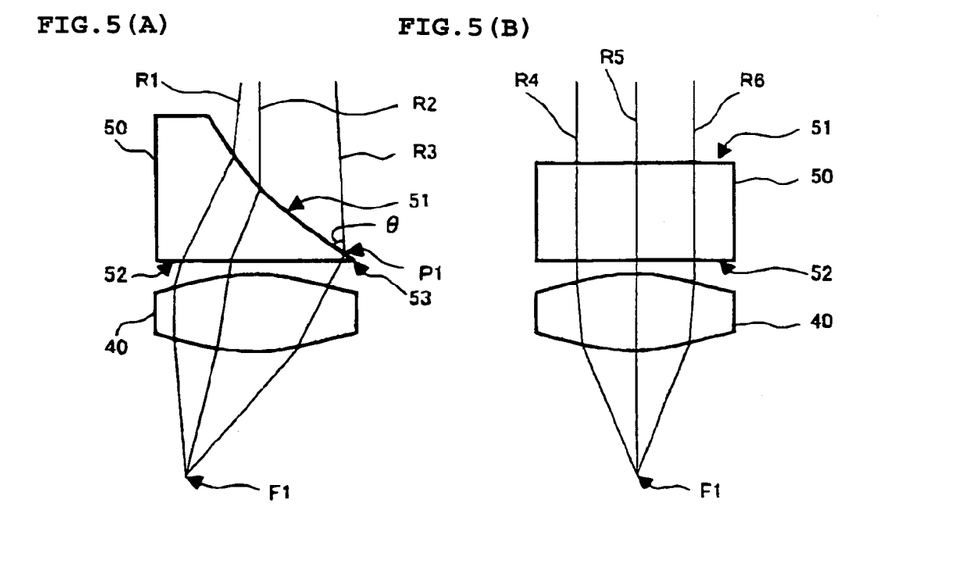
FIG. 5A is a partially enlarged side view showing the front lens and the observation prism of FIG. 4
FIG. 5B is a cross sectional view in a direction orthogonal to a paper surface in FIG. 5A.
Figure 6:
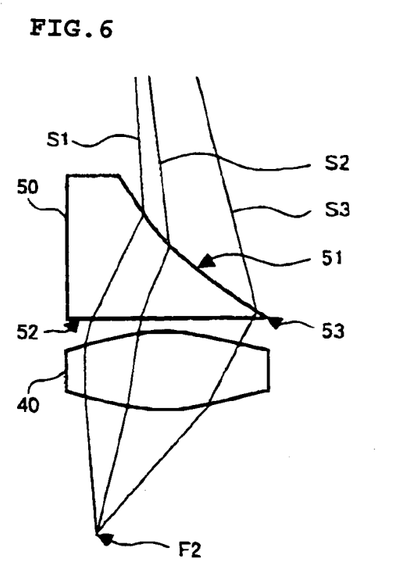
FIG. 6 is an explanatory view showing an imaging state of an exit pupil of an illumination system in the case where the fundus and its surroundings of the eye to be operated are being observed with the state in which the observation prism is disposed.

Next, a structure and an operation of the observation prism used in the case where a vitreous body operation is conducted on the eye to be operated E using the operation microscope 1 will be described with reference to FIGS. 4, 5A, 5B, and 6. FIG. 4 is a schematic view showing an imaging state of the entrance pupil of the observation system in the case where fundus and its surroundings Er' of the eye to be operated E are being observed in a state where the observation prism 50 according to this embodiment is disposed. In FIG. 4, reference symbol P denotes a point on a cornea of the eye to be operated E which is conjugate with the entrance pupil of the observation system. FIGS. 5A and 5B are partially enlarged views showing the front lens 40 and the observation prism 50 which are shown in FIG. 4. FIG. 5A is a side view and FIG. 5B is a cross sectional view in a direction orthogonal to a paper surface of FIG. 5A. FIG. 6 is an explanatory view showing an imaging state of the exit pupil of the illumination system in the case where the fundus and its surroundings Er' of the eye to be operated E are being observed in a state where the observation prism 50 is disposed.

The observation prism 50 is disposed between the anterior focal point F of the objective lens 11 and the front lens 40. Here, reference symbol F' denotes an intermediate image plane on which an image of the fundus Er (or the fundus and its surroundings Er') of the eye to be operated E is formed. Although not shown, the observation prism 50 is stored in a predetermined case and disposed at the above-mentioned position by fitting the lower portion of the predetermined case to the upper portion of the holding plate 41a of the front lens 40.

As shown in FIG. 5A, in the observation prism 50 provided in the operation microscope 1 according to this embodiment, the illumination light and observation light are refracted on two refractive surfaces 51 and 52 which intersect each other at an intersection (prism apex) 53. The refractive surface 52 is formed flat.

The refractive surface (also called an oblique surface) 51 has a curved shape in which an inclination angle of the tangent of the oblique surface to the refractive surface 52 gradually becomes smaller in a direction to the intersection 53, that is, a concave shape. (Or the oblique surface 51 shows a certain negative curvature in the direction to the intersection 53.) Here, in order to clearly show the structure of the observation prism, the curvature of the refractive surface 51 is exaggerated in FIGS. 4 and 5A.

As shown in FIG. 5B, the curvature of the oblique surface 51 along a direction orthogonal to the oblique direction (direction orthogonal to a paper surface in FIG. 5A) is 0. That is, the oblique surface 51 constitutes (portion of) a cylinder surface in which the curvature along the oblique direction takes a predetermined (negative) value and the curvature along the direction orthogonal to the oblique direction is 0. Although a modified example is described later, the structure of the observation prism 50 is not limited to this.

The curvature of the refractive surface 51 of the observation prism 50 can be determined as appropriate based on a result obtained by calculating the amount of aberration caused when the oblique surface is assumed to be flat.

A problem inherent in the conventional operation microscope shown in FIGS. 8 and 9A will be described. Here, the front lens 103 has a refractive lens 103a on the observation prism 102 side and a refractive surface 103b on the side of the eye to be operated E. In the conventional operation microscope, particularly, the principle ray R3 transmitted through the vicinity of the prism apex 102c is incident on the refraction surface 103b (on the side of the eye to be operated E) of the front lens 103 from an extremely oblique direction, so that a large aberration is caused.

On the other hand, in the operation microscope according to this embodiment, the negative curvature is provided in the curved direction (direction where aberration is caused) of the refractive surface 51 of the observation prism 50. Therefore, the principle ray R3 transmitted through the vicinity of the prism apex 53 is incident on the observation prism 50 at a large angle θ as compared with a conventional case, so that an aberration is less caused than the conventional case. An aberration reverse to aberrations caused at incident points of the principle rays R1 and R2 is caused at an incident point P1 of the principle ray R3.

Thus, the aberrations caused when the front lens 40 and the observation prism 50 are used are corrected to suitably condense the respective principle rays R1 to R3 at a point F1. Here, assume that the operator's microscope 6 is driven in advance by the drive device 5 to perform an alignment with the eye to be operated E, thereby aligning the condensing point F1 of the principle rays R1 to R3 with the point P on the cornea (point conjugate with the entrance pupil of the observation system). Therefore, as shown in FIG. 4, a preferable imaging state in which an aberration is less can be obtained. When such an imaging state is obtained, as shown in FIG. 10A, the images A' of the entrance pupils of the right and left observation systems are sufficiently separated from each other on the cornea C of the eye to be operated E, so that the glare can be prevented from occurring. Note that the aberration is not caused in the direction orthogonal to the curved direction of the refractive surface 51 because the curvature along the curved direction of the refractive surface 51 shows 0 (see FIG. 5B).

FIG. 6 is an explanatory view showing an imaging state of the exit pupil of the illumination system in the case where the fundus and its surroundings Er' of the eye to be operated E are being observed with the state in which the observation prism 50 is disposed as described above, which is a side view showing the front lens 40 and the observation prism 50 (corresponds to FIG. 5A).

Figure 3:
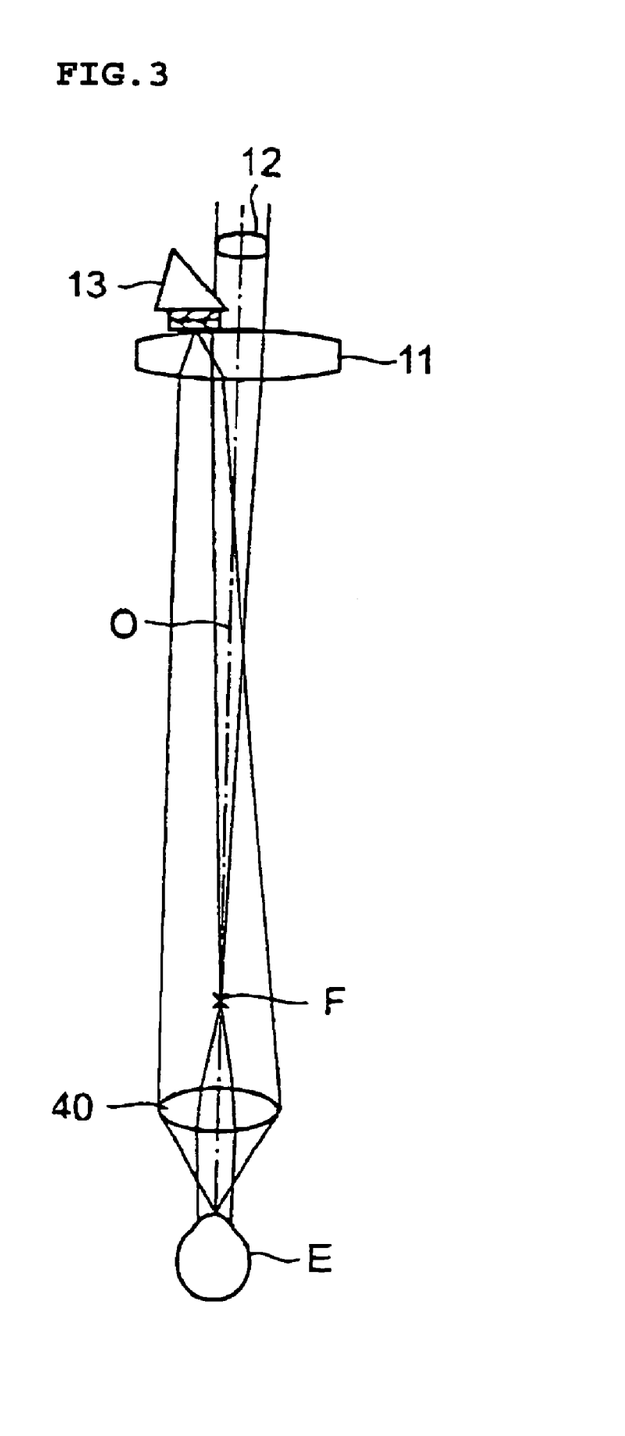
FIG. 3 is a schematic view showing a part of an optical system included in the operation microscope according to the embodiment of the present invention.

As shown in FIG. 3, illumination light guided from the illumination system (not shown) through the illumination prism 13 and the objective lens 11 is projected to the eye to be operated E from a predetermined angle direction with respect to the observation axis O. Here, when the conventional observation prism 102 is used, the illumination light (particularly, a light beam on the prism apex 53 side, which is far from the illumination prism 13) is incident on the front lens 40 from an extremely oblique direction. Therefore, a large aberration is caused, so that the image of the exit pupil of the illumination system on the cornea of the eye to be operated E is formed as the image B' shown in FIG. 10B in a blurred state with the large amount of aberration.

On the other hand, when the observation prism 50 having the refractive surface 51 serving as the cylinder-curved surface according to this embodiment is disposed, optical paths of principle rays S1 to S3 of the illumination light are formed as shown in FIG. 6. In particular, the principle ray S3 is incident on the observation prism 50 at an angle larger than that in a conventional case with respect to the refractive surface 51, so that the amount of aberration caused on the refractive surface 51 reduces and an aberration reverse to aberrations caused at incident points of the principle rays S1 and S2 is caused, thereby correcting the aberration as a whole. Thus, the image of the exit pupil of the illumination system is clearly formed as the image B shown in FIG. 10A on the cornea of the eye to be operated E.

As described above, the observation prism 50 having the concave refractive surface 51 for generating negative refracting power in the curved direction (direction where aberration is caused) is used as in this embodiment. Therefore, the images A of the entrance pupils of the observation system and the image B of the exit pupil of the illumination system are preferably formed on the cornea of the eye to be operated E in a state where the aberrations are corrected. Thus, as shown in FIG. 10A, the images A of the entrance pupils of the observation system and the image B of the exit pupil of the illumination system are sufficiently separated from one another, so that a suitable observation state with less glare can be obtained.

MODIFIED EXAMPLE

Figures 7A, 7B:
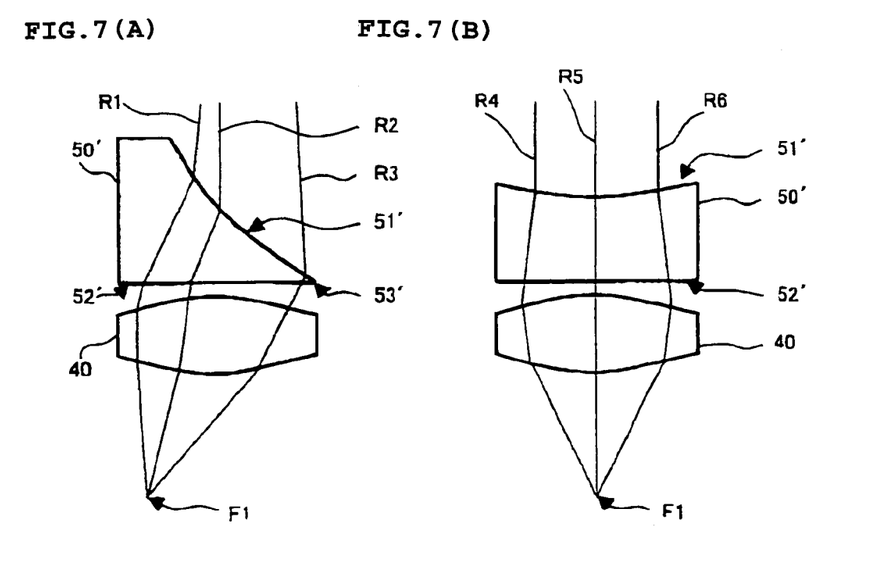
FIG. 7A is a partially enlarged side view showing a modified example of the operation microscope according to the embodiment of the present invention and FIG. 7B is a cross sectional view in a direction orthogonal to a paper surface of FIG. 7A.

The observation prism used for the operation microscope 1 is not limited to a structure having the cylinder-curved oblique surface as described above and may be a prism having, for example, a toric-curved oblique surface. As shown in FIG. 7A, an observation prism 50' includes a toric-curved oblique surface 51' having a curvature for generating negative refracting power in an oblique direction and a curvature for generating negative refracting power in a direction orthogonal to the oblique direction. According to the observation prism 50', the aberration caused in the oblique direction can be corrected. In addition, the observation prism 50' has a function as a magnification changing lens. Note that the curvature along the direction orthogonal to the oblique direction may be one for generating positive refracting power. That is, in the case of an observation prism including an oblique surface having negative refracting power for correcting the aberration in the oblique direction, the curvature along the direction orthogonal to the oblique direction can be arbitrarily set according to purposes.

The structure described above in detail is presented as an example for embodying the present invention and therefore various structural modifications, changes, and additions can be made without departing from the scope of the present invention. For example, an observation prism in which a refractive surface on a lower surface side (front lens side) is formed in a concave shape or an observation prism in which each of two refractive surfaces are formed in a concave shape may be used. Such observation prisms can be applied to an observation using a desirable observation apparatus other than the operation microscope. For example, when the observation prism of the present invention is used to change an illumination region of an object to be observed, it is possible to correct the aberrations caused when the illumination light and the observation light are refracted.

According to an operation microscope according to a first aspect of the present invention, the aberration caused when the fundus and its surroundings are observed using the observation prism is corrected. Therefore, the imaging states of the images of the entrance pupils of the observation system and the imaging state of the image of the exit pupil of the illumination system are improved, so that a high-visibility observation with less glare can be conducted.

Also, according to an observation prism according to a fourth aspect of the present invention, when the observation prism is used for an operation microscope in the ophthalmologic field, the aberration caused when the fundus and its surroundings are observed is corrected. Therefore, the imaging states of the images of the entrance pupils of the observation system and the imaging state of the image of the exit pupil of the illumination system are improved, so that a high-visibility observation with less glare can be conducted.

What is claimed is:

1. An operation microscope, comprising:
   an objective lens opposed to an eye to be operated;
   a front lens for condensing illumination light to illuminate an interior of the eye to be operated, which is removably inserted between the eye to be operated and an anterior focal point of the objective lens; and
   an observation prism for refracting the illumination light on two refractive surfaces to illuminate fundus and its surroundings of the eye to be operated, which is removably inserted between the anterior focal point of the objective lens and the front lens,
   wherein the operation microscope is characterized in that at least one of the two refractive surfaces of the observation prism is formed in a curved shape in which said curved shape shows a certain negative curvature in a direction to an intersection of the two refractive surfaces.

2. An operation microscope according to the claim 1, wherein said certain negative curvature is variable negative curvature.

3. An operation microscope according to claim 1, wherein the operation microscope is characterized in that one of the two refractive surfaces of the observation prism is formed in the curved shape in which a curvature along a direction orthogonal to the direction to the intersection shows 0.

4. An operation microscope according to claim 1, wherein the operation microscope is characterized in that one of the two refractive surfaces of the observation prism is formed in the curved shape in which the curved shape shows a negative curvature at a constant rate in the direction to the intersection.

5. An observation prism which is disposed between an anterior focal point of an objective lens and a front lens of an operation microscope including the front lens for condensing illumination light to illuminate an interior of an eye to be operated, the front lens being provided between the eye to be operated and the anterior focal point of the objective lens, and used for refracting the illumination light on two refractive surfaces to illuminate fundus and its surroundings of the eye to be operated,
   wherein the observation prism is characterized in that at least one of the two refractive surfaces is formed in a curved shape in which said curved shape shows a certain negative curvature in a direction to an intersection of the two refractive surfaces.

* * * * *